United States Patent
Canfield et al.

(10) Patent No.: US 10,010,373 B2
(45) Date of Patent: Jul. 3, 2018

(54) NAVIGATION SYSTEM FOR CARDIAC THERAPIES USING GATING

(71) Applicant: Medtronic, Inc., Minneapolis, MN (US)

(72) Inventors: Monte R Canfield, Center City, MN (US); Michael R Neidert, San Francisco, CA (US); Kenneth C Gardeski, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/368,128

(22) Filed: Dec. 2, 2016

(65) Prior Publication Data
US 2017/0189124 A1 Jul. 6, 2017

Related U.S. Application Data

(63) Continuation of application No. 12/183,688, filed on Jul. 31, 2008.

(51) Int. Cl.
*A61B 34/20* (2016.01)
*A61B 5/0456* (2006.01)
(Continued)

(52) U.S. Cl.
CPC .......... *A61B 34/20* (2016.02); *A61B 5/0066* (2013.01); *A61B 5/036* (2013.01); *A61B 5/0456* (2013.01); *A61B 5/4839* (2013.01); *A61B 6/032* (2013.01); *A61B 6/037* (2013.01); *A61B 6/541* (2013.01); *A61B 8/0841* (2013.01); *A61B 8/12* (2013.01);
(Continued)

(58) Field of Classification Search
CPC ............................... A61B 6/541; A61B 34/20
See application file for complete search history.

(56) References Cited

U.S. PATENT DOCUMENTS

| | | |
|---|---|---|
| 3,939,824 A | 2/1976 | Arneson et al. |
| 4,181,135 A | 1/1980 | Andresen et al. |

(Continued)

FOREIGN PATENT DOCUMENTS

EP 1421913 A1 5/2004

OTHER PUBLICATIONS (PCT/US2009/050795) PCT Notification of Transmittal of the International Search Report and the Written Opinion of the International Searching Authority, dated Jan. 12, 2010, 12 pages.

(Continued)

*Primary Examiner* — Tse Chen
*Assistant Examiner* — Jason Ip (57) ABSTRACT

An image guided navigation system for navigating a region of a patient which is gated using ECG signals to confirm diastole. The navigation system includes an imaging device, a tracking device, a controller, and a display. The imaging device generates images of the region of a patient. The tracking device tracks the location of the instrument in a region of the patient. The controller superimposes an icon representative of the instrument onto the images generated from the imaging device based upon the location of the instrument. The display displays the image with the superimposed instrument. The images and a registration process may be synchronized to a physiological event.

12 Claims, 7 Drawing Sheets

(51) Int. Cl.

| | | |
|---|---|---|
| *A61B 5/00* | (2006.01) | |
| *A61B 6/03* | (2006.01) | |
| *A61B 8/08* | (2006.01) | |
| *A61B 8/12* | (2006.01) | |
| *A61N 1/372* | (2006.01) | |
| *A61B 5/03* | (2006.01) | |
| *A61M 25/01* | (2006.01) | |
| *A61B 8/00* | (2006.01) | |
| *A61B 6/00* | (2006.01) | |
| *A61M 25/09* | (2006.01) | |
| *A61B 18/14* | (2006.01) | |
| *A61B 90/00* | (2016.01) | |
| *A61B 18/00* | (2006.01) | |

(52) U.S. Cl.
CPC .......... *A61B 8/543* (2013.01); *A61B 18/1492* (2013.01); *A61M 25/0108* (2013.01); *A61M 25/09* (2013.01); *A61N 1/372* (2013.01); *A61B 2018/00577* (2013.01); *A61B 2018/00839* (2013.01); *A61B 2034/2063* (2016.02); *A61B 2034/2065* (2016.02); *A61B 2090/374* (2016.02); *A61B 2090/3735* (2016.02); *A61B 2090/3764* (2016.02); *A61B 2090/3784* (2016.02); *A61M 2230/04* (2013.01)

(56) References Cited

U.S. PATENT DOCUMENTS

| | | | |
|---|---|---|---|
| 4,259,966 | A | 4/1981 | Cannon et al. |
| 4,336,810 | A * | 6/1982 | Anderson .......... A61B 5/04365 |
| | | | 600/515 |
| 4,393,877 | A | 7/1983 | Imran et al. |
| 4,419,998 | A | 12/1983 | Heath |
| 4,446,873 | A | 5/1984 | Groch et al. |
| 4,694,837 | A | 9/1987 | Blakeley et al. |
| 5,113,869 | A | 5/1992 | Nappholz et al. |
| 5,592,939 | A | 1/1997 | Martinelli |
| 5,740,808 | A | 4/1998 | Panescu et al. |
| 5,913,820 | A | 6/1999 | Bladen et al. |
| 5,935,160 | A | 8/1999 | Anricchio et al. |
| 5,983,126 | A | 11/1999 | Wittkampf |
| 6,118,845 | A | 9/2000 | Simon et al. |
| 6,192,280 | B1 | 2/2001 | Sommer et al. |
| 6,381,485 | B1 | 4/2002 | Hunter et al. |
| 6,470,207 | B1 | 10/2002 | Simon et al. |
| 6,556,695 | B1 | 4/2003 | Packer et al. |
| 6,708,052 | B1 | 3/2004 | Mao et al. |
| 6,950,689 | B1 | 9/2005 | Willis et al. |
| 7,697,972 | B2 | 4/2010 | Verard et al. |
| 2003/0114749 | A1 | 6/2003 | Rahn |
| 2004/0077941 | A1 | 4/2004 | Reddy et al. |
| 2004/0097805 | A1 | 5/2004 | Verard et al. |
| 2004/0176681 | A1 | 9/2004 | Mao et al. |
| 2004/0215071 | A1 | 10/2004 | Frank et al. |
| 2004/0215671 | A1 | 10/2004 | Hyakutake et al. |
| 2005/0038337 | A1 | 2/2005 | Edwards |
| 2006/0079759 | A1 | 4/2006 | Vaillant et al. |
| 2006/0173373 | A1 | 8/2006 | Shin et al. |
| 2008/0111546 | A1 * | 5/2008 | Takahashi .............. A61B 5/055 |
| | | | 324/307 |
| 2010/0030061 | A1 | 2/2010 | Canfield et al. |

OTHER PUBLICATIONS

Champleboux et al., "Accurate Calibration of Cameras and Range Imaging Sensors: the NPBS Method," IEEE International Conference on Robotics and Automation, Nice, France, May 1992.

Schueler et al., "Correction of Image Intensifier Distortion for Three-Dimensional X-Ray Anigiography," SPIE Medical Imaging 1995, vol. 2432, DD. 272-279.

Degen, Thomas et al., "A Pseudodifferential Amplifier for Bioelectric Events With DC-Offset Compensation Using Two-Wired Amplifying Electrodes", IEEE Transactions on Biomedical Engineering, vol. 53, No. 2, Feb. 2006, pp. 300-310.

* cited by examiner

FIGURE 7

NAVIGATION SYSTEM FOR CARDIAC THERAPIES USING GATING

RELATED APPLICATION

This application is a continuation of U.S. patent application Ser. No. 12/183,688, filed Jul. 31, 2008 entitled "NAVIGATION SYSTEM FOR CARDIAC THERAPIES USING GATING", which is herein incorporated by reference in its entirety.

FIELD OF THE INVENTION

The present invention relates generally to image guided surgery, and more specifically, to systems and methods for using one or more medical images to assist in navigating an instrument through internal body structures, in particular for navigating a catheter in a moving body structure, such as the heart, during a surgical procedure.

BACKGROUND OF THE INVENTION

Image guided medical and surgical procedures utilize patient images obtained prior to or during a medical procedure to guide a physician performing the procedure. Recent advances in imaging technology, especially in imaging technologies that produce two, three, and four dimensional images, such as computed tomography (CT), magnetic resonance imaging (MRI), isocentric C-arm fluoroscopic imaging, positron emission tomography (PET), and ultrasound imaging (US), has increased the interest in image guided medical procedures.

At present, cardiac catheterization procedures are typically performed with the aid of fluoroscopic images. Two-dimensional fluoroscopic images taken intra-procedurally allow a physician to visualize the location of a catheter being advanced through cardiovascular structures. However, use of such fluoroscopic imaging throughout a procedure exposes both the patient and the operating room staff to radiation, and exposes the patient to contrast agents. Therefore, the number of fluoroscopic images taken during a procedure is preferably limited to reduce the radiation exposure to the patient and staff.

An image guided surgical navigation system that enables the physician to see the location of an instrument relative to a patient's anatomy, without the need to acquire real-time fluoroscopic images throughout the surgical procedure is generally disclosed in U.S. Pat. No. 6,470,207, entitled "Navigational Guidance Via Computer-Assisted Fluoroscopic Imaging," issued Oct. 22, 2002, which is incorporated herein by reference in its entirety. In this system, representations of surgical instruments are overlaid on pre-acquired fluoroscopic images of a patient based on the position of the instruments determined by a tracking sensor.

Other types of procedures include the use of electro-physiologic mapping catheters to map the heart based on measured electrical potentials. Such mapping catheters are useful in identifying an area of tissue that is either conducting normally or abnormally, however, some mapping catheters may not aid in actually guiding a medical device to a targeted tissue area for medical treatment.

Other procedures that could benefit from a navigation system include cardiac lead placement. Cardiac lead placement is important in achieving proper stimulation or accurate sensing at a desired cardiac location. Endocardial is one type of lead placement procedure that is an internal procedure where coronary vein leads are generally implanted with the use of a guide catheter and/or a guide wire or stylet to achieve proper placement of the lead. Epicardial is another type of procedure that is an external procedure for cardiac lead placement that may also benefit from this navigation system. A coronary vein lead may be placed using a multi-step procedure wherein a guide catheter is advanced into the coronary sinus ostium and a guide wire is advanced further through the coronary sinus and great cardiac vein to a desired cardiac vein branch. Because the tip of a guide wire is generally flexible and may be preshaped in a bend or curve, the tip of the guide wire can be steered into a desired venous branch. The guide wire tip is directed with a steerable guide catheter, and with the appropriate pressure, it is manipulated into the desired vein branch.

A cardiac lead may therefore be advanced to a desired implant location using a guide wire extending entirely through the lead and out its distal end. Cardiac leads generally need to be highly flexible in order to withstand flexing motion caused by the beating heart without fracturing. A guide wire provides a flexible lead with the stiffness needed to advance it through a venous pathway. Leads placed with the use of a guide wire are sometimes referred to as "over-the-wire" leads. Once the lead is placed in a desired location, the guide wire and guide catheter may be removed. A guide wire placed implantable lead is disclosed in U.S. Pat. No. 6,192,280, entitled "Guide wire Placed Implantable Lead With Tip Seal," issued Feb. 20, 2001. A coronary vein lead having a flexible tip and which may be adapted for receiving a stylet or guide wire is disclosed in U.S. Pat. No. 5,935,160, entitled "Left Ventricular Access Lead for Heart Failure Pacing", issued Aug. 10, 1999, each of which are hereby incorporated by reference.

Also, pacing lead procedures currently performed today for use in heart failure treatment are not optimized. In this regard, the lead placement is not optimized due to the lack of having real-time anatomic information, navigation and localization information, hemo-dynamic data, and electro-physiological data. Currently, pacing leads are simply "stuffed" into the heart without any optimization being performed due to lack of information that can be used for this optimization.

Advancement of a guide catheter or an over-the-wire lead through a vessel pathway and through cardiac structures requires considerable skill and can be a time-consuming task. This type of procedure also exposes the patient to an undesirable amount of radiation exposure and contrast agent. Therefore, it is desirable to provide an image guided navigation system that allows the location of a guide catheter being advanced within the cardiovascular structures for lead placement to be followed in either two, three, or four dimensional space in real time. It is also desirable to provide an image guided navigation system that assists in navigating an instrument, such as a catheter, through a moving body structure or any type of soft tissue.

With regard to navigating an instrument through a moving body structure, difficulties arise in attempting to track such an instrument using known tracking technology as the instrument passes adjacent or through a moving body structure, since the virtual representation of the instrument may be offset from the corresponding anatomy when superimposed onto image data. Accordingly, it is also desirable to acquire image data and track the instrument in a synchronized manner with the pre-acquired image using gating or synchronization techniques, such as ECG gating or respiratory gating.

Other difficulties with cardiac procedures include annual check-ups to measure early indications for organ rejection in heart transplant patients. These indicators include white blood cells, chemical change, blood oxygen levels, etc. During the procedure, an endovascular biopsy catheter is inserted into the heart and multiple biopsies are performed in the septum wall of the heart. Again, during this procedure, radiation and contrast agent is utilized to visualize the biopsy catheter, thereby exposing both a patient and the doctor to potential excess radiation and contrast agents during the procedure. As such, it would also be desirable to provide an image guided navigation system that assists in performing this type of procedure in order to reduce radiation and contrast agent exposure.

SUMMARY OF THE INVENTION

A navigation system is provided including a catheter carrying single or multiple localization sensors, a sensor interface, a user interface, a controller, and a visual display. Aspects of the present invention allow for the location of a catheter advanced within an internal space within the human body, for example within the cardiovascular structures, to be identified in two, three or four dimensions in real time. Further aspects of the present invention allow for accurate mapping of a tissue or organ, such as the heart or other soft tissue, and/or precise identification of a desired location for delivering a medical lead, or other medical device or therapy, while reducing the exposure to fluoroscopy normally required during conventional catheterization procedures. These types of therapies include, but are not limited to, drug delivery therapy, cell delivery therapy, ablation, stenting, or sensing of various physiological parameters with the appropriate type of sensor. In cardiac applications, methods included in the present invention compensate for the effects of respiration and the beating heart that can normally complicate mapping or diagnostic data. Aspects of the present invention may be tailored to improve the outcomes of numerous cardiac therapies as well as non-cardiac therapies, such as neurological, oncological, or other medical therapies, including lung, liver, prostate and other soft tissue therapies, requiring the use of a catheter or other instrument at a precise location.

The steerable catheter provided by the present invention features at least one or more location sensors located near the distal end of an elongated catheter body. The location sensors may be spaced axially from each other and may be electromagnetic detectors. An electromagnetic source is positioned externally to the patient for inducing a magnetic field, which causes voltage to be developed on the location sensors. The location sensors may each be electrically coupled to twisted pair conductors, which extend through the catheter body to the proximal catheter end. Twisted pair conductors provide electromagnetic shielding of the conductors, which prevents voltage induction along the conductors when exposed to the magnetic flux produced by the electromagnetic source. Alternatively, the sensors and the source may be reversed where the catheter emits a magnetic field that is sensed by external sensors.

By sensing and processing the voltage signals from each location sensor, the location of the catheter tip with respect to the external sources and the location of each sensor with respect to one another may be determined. The present invention allows a two, three, or four-dimensional reconstruction of several centimeters of the distal portion of the catheter body in real time. Visualization of the shape and position of a distal portion of the catheter makes the advancement of the catheter to a desired position more intuitive to the user. The system may also provide a curve fitting algorithm that is selectable based upon the type of catheter used, and based upon the flexibility of the catheter, based upon a path finding algorithm, and based upon image data. This enables estimated curved trajectories of the catheter to be displayed to assist the user.

The location sensor conductors, as well as conductors coupled to other physiological sensors present, are coupled to a sensor interface for filtering, amplifying, and digitizing the sensed signals. The digitized signals are provided via a data bus to a control system, embodied as a computer. Programs executed by the control system process the sensor data for determining the location of the location sensors relative to a reference source. A determined location is superimposed on a two, three, or four-dimensional image that is displayed on a monitor. A user-interface, such as a keyboard, mouse or pointer, is provided for entering operational commands or parameters.

In one embodiment, an image guided navigation system for guiding an instrument through a region of the patient includes an anatomic gating device, an imaging device, a tracking device, a controller, and a display. The anatomic gating device senses a first and second physiological event. The imaging device captures image data in response to the first and second physiological event. The tracking device tracks the position of the instrument in the region of the patient. The controller is in communication with the anatomic gating device, the imaging device and the tracking device, and registers the image data with the region of a patient in response to the first and second physiological event. The controller also superimposes an icon representing the instrument onto the image data, based on the tracked position. The display shows the image data of the region of the patient with the superimposed icon of the instrument.

Further areas of applicability of the present invention will become apparent from the detailed description provided hereinafter. It should be understood that the detailed description and specific examples, while indicating the preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses. As indicated above, the present invention is directed at providing improved, non-line-of-site, image-guided navigation of an instrument, such as a catheter, balloon catheter, implant, lead, stent, needle, guide wire, insert, and/or capsule, that may be used for physiological monitoring, delivering a medical therapy, or guiding the delivery of a medical device in an internal body space, such as the heart or any other region of the body.

Figure 1:
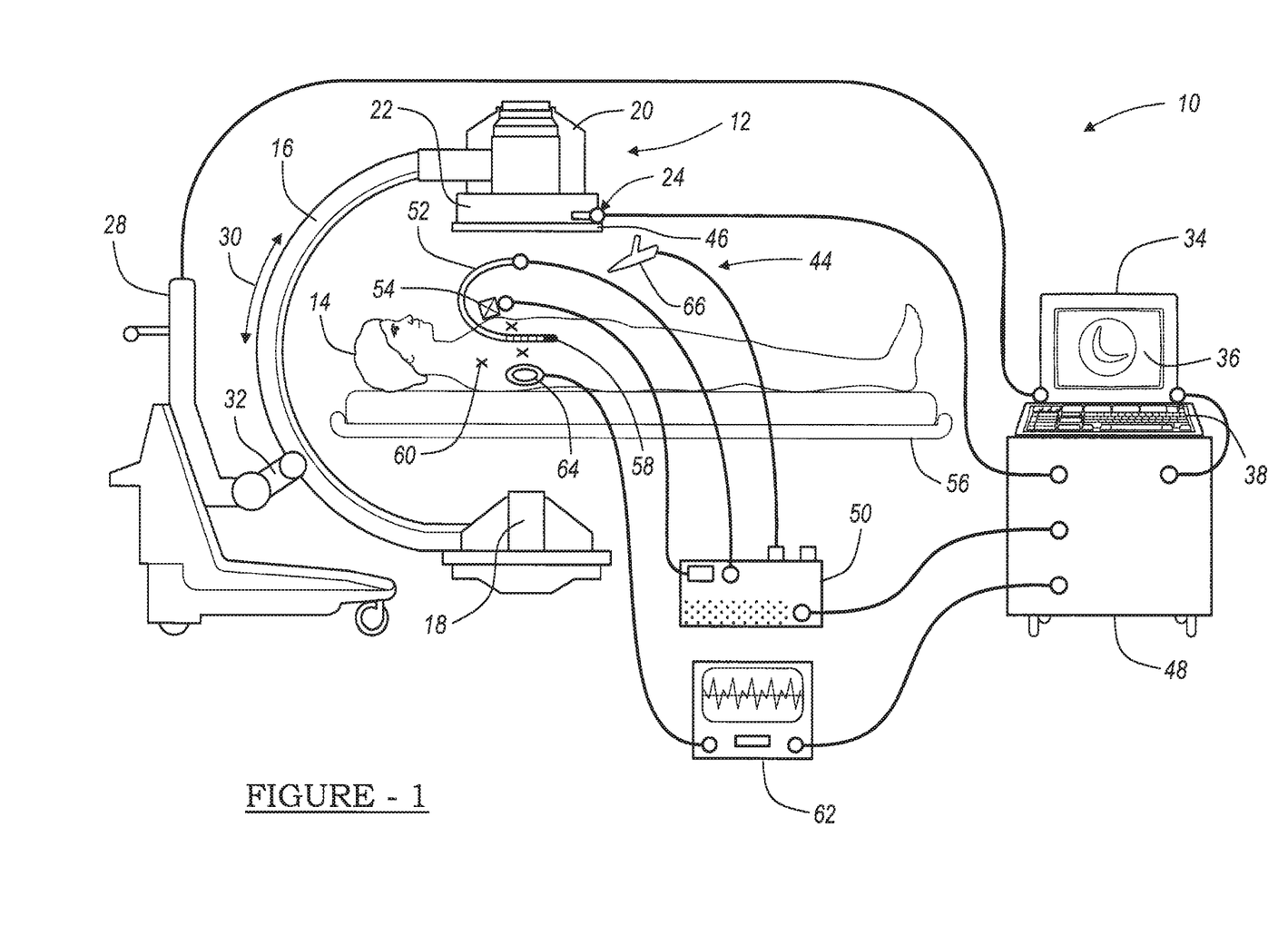
FIG. 1 is a diagram of a catheter navigation system according to the teachings of the present invention.

FIG. 1 is a diagram illustrating an overview of an image-guided catheter navigation system 10 for use in non-line-of-site navigating of a catheter during cardiac therapy or any other soft tissue therapy. It should further be noted that the navigation system 10 may be used to navigate any other type of instrument or delivery system, including guide wires, needles, drug delivery systems, cell delivery systems, gene delivery systems, and biopsy systems. Moreover, these instruments may be used for cardiac therapy or any other therapy in the body or be used to navigate or map any other regions of the body, such as moving body structures. However, each region of the body poses unique requirements to navigate, as disclosed herein. For example, the navigation system 10 addresses multiple cardiac, neurological, organ and other soft tissue therapies, including drug delivery, cell transplantation, gene delivery, electro-physiology ablations, revascularization, biopsy guidance, mitral valve repair, aortic valve repair, leadless pacemaker placement, leadless pressure sensor placement, and virtual echography imaging.

The navigation system 10 may include an imaging device 12 that is used to acquire pre-operative or real-time images of a patient 14. The imaging device 12 is a fluoroscopic x-ray imaging device that may include a C-arm 16 having an x-ray source 18, an x-ray receiving section 20, an optional calibration and tracking target 22, and optional radiation sensors 24. The calibration and tracking target 22 includes calibration markers 26 (see FIGS. 2a-2b), further discussed herein. A C-arm controller 28 captures the x-ray images received at the receiving section 20 and stores the images for later use. The C-arm controller 28 may also control the rotation of the C-arm 16. For example, the C-arm 16 may move in the direction of arrow 30 or rotates about the long axis of the patient, allowing anterior or lateral views of the patient 14 to be imaged. Each of these movements involve rotation about a mechanical axis 32 of the C-arm 16. In this example, the long axis of the patient 14 is substantially in line with the mechanical axis 32 of the C-arm 16. This enables the C-arm 16 to be rotated relative to the patient 14, allowing images of the patient 14 to be taken from multiple directions or about multiple planes. An example of a fluoroscopic C-arm x-ray imaging device 12 is the "Series 9600 Mobile Digital Imaging System," from OEC Medical Systems, Inc., of Salt Lake City, Utah. Other exemplary fluoroscopes include bi-plane fluoroscopic systems, ceiling fluoroscopic systems, cath-lab fluoroscopic systems, fixed C-arm fluoroscopic systems, isocentric C-arm fluoroscopic systems, 3D fluoroscopic systems, etc.

In operation, the imaging device 12 generates x-rays from the x-ray source 18 that propagate through the patient 14 and calibration and/or tracking target 22, into the x-ray receiving section 20. The receiving section 20 generates an image representing the intensities of the received x-rays. Typically, the receiving section 20 includes an image intensifier that first converts the x-rays to visible light and a charge coupled device (CCD) video camera that converts the visible light into digital images. Receiving section 20 may also be a digital device that converts x-rays directly to digital images, thus potentially avoiding distortion introduced by first converting to visible light. With this type of digital C-arm, which is generally a flat panel device, the optional calibration and/or tracking target 22 and the calibration process discussed below may be eliminated. Also, the calibration process may be eliminated or not used at all for cardiac therapies. Alternatively, the imaging device 12 may only take a single image with the calibration and tracking target 22 in place. Thereafter, the calibration and tracking target 22 may be removed from the line-of-sight of the imaging device 12.

Two-dimensional fluoroscopic images taken by the imaging device 12 are captured and stored in the C-arm controller 28. Multiple two-dimensional images taken by the imaging device 12 may also be captured and assembled to provide a larger view or image of a whole region of a patient, as opposed to being directed to only a portion of a region of the patient. For example, multiple image data of a patient's leg may be appended together to provide a full view or complete set of image data of the leg that can be later used to follow a contrast agent, such as Bolus tracking. These images are then forwarded from the C-arm controller 28 to a controller or work station 34 having a display 36 and a user interface 38. The work station 34 provides facilities for exhibiting on the display 36, and saving, digitally manipulating, or printing a hard copy of the received images. The user interface 38, which may be a keyboard, mouse, touch pen, touch screen or other suitable device, allows a physician or user to provide inputs to control the imaging device 12 via the C-arm controller 28, or adjust the display settings of the display 36. The work station 34 may also direct the C-arm controller 28 to adjust the rotational axis 32 of the C-arm 16 to obtain various two-dimensional images along different planes in order to generate representative two-dimensional and three-dimensional images. When the x-ray source 18 generates the x-rays that propagate to the x-ray receiving section 20, the radiation sensors 24 sense the presence of radiation, which is forwarded to the C-arm controller 28 to identify whether or not the imaging device 12 is actively imaging. This information is also transmitted to a coil array controller 48, further discussed herein. Alternatively, a person or physician may manually indicate when the imaging device 12 is actively imaging or this function can be built into the x-ray source 18, x-ray receiving section 20, or the control computer 28.

Figure 2A:
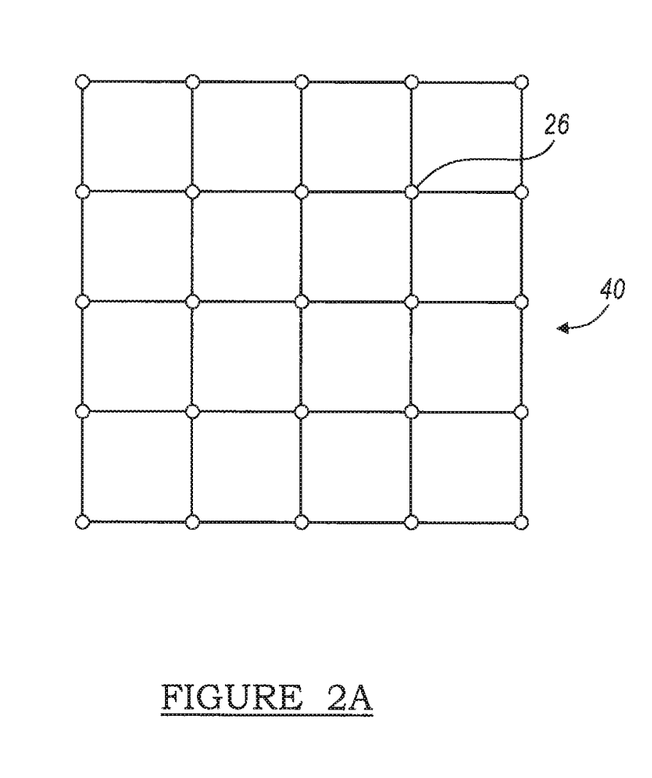
FIGS. 2a and 2b are diagrams representing undistorted and distorted views from a fluoroscopic C-arm imaging device.
Figure 2B:
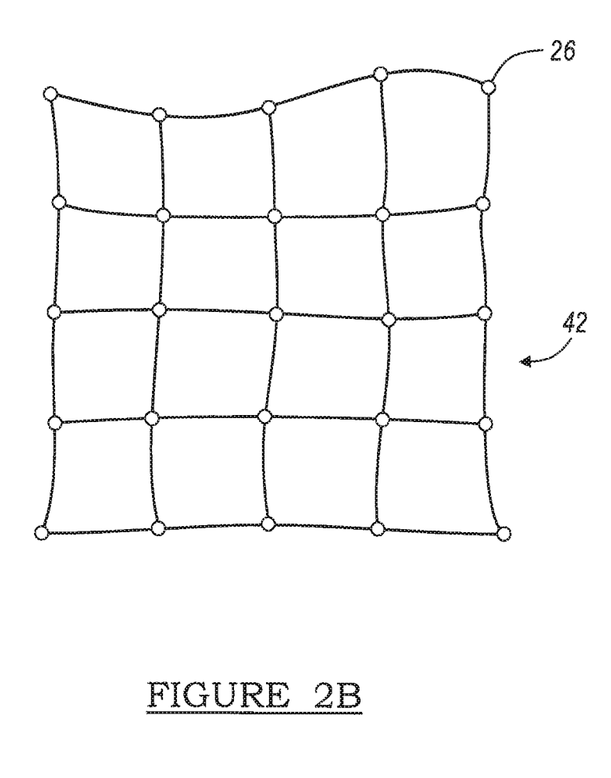

Fluoroscopic C-arm imaging devices 12 that do not include a digital receiving section 20 generally require the optional calibration and/or tracking target 22. This is because the raw images generated by the receiving section 20 tend to suffer from undesirable distortion caused by a number of factors, including inherent image distortion in the image intensifier and external electromagnetic fields. An empty undistorted or ideal image and an empty distorted image are shown in FIGS. 2a and 2b, respectively. The checkerboard shape, shown in FIG. 2a, represents the ideal image 40 of the checkerboard-arranged calibration markers 26. The image taken by the receiving section 20, however, can suffer from distortion, as illustrated by the distorted calibration marker image 42, shown in FIG. 2b.

Intrinsic calibration, which is the process of correcting image distortion in a received image and establishing the projective transformation for that image, involves placing the calibration markers 26 in the path of the x-ray, where the calibration markers 26 are opaque or semi-opaque to the x-rays. The calibration markers 26 are rigidly arranged in pre-determined patterns in one or more planes in the path of the x-rays and are visible in the recorded images. Because the true relative position of the calibration markers 26 in the recorded images are known, the C-arm controller 28 or the work station or computer 34 is able to calculate an amount of distortion at each pixel in the image (where a pixel is a single point in the image). Accordingly, the computer or work station 34 can digitally compensate for the distortion in the image and generate a distortion-free or at least a distortion-improved image 40 (see FIG. 2a). A more detailed explanation of exemplary methods for performing intrinsic calibration is described in the references: B. Schuele, et al., "Correction of Image Intensifier Distortion for Three-Dimensional Reconstruction," presented at SPIE Medical Imaging, San Diego, Calif., 1995; G. Champleboux, et al., "Accurate Calibration of Cameras and Range Imaging Sensors: the NPBS Method," Proceedings of the IEEE International Conference on Robotics and Automation, Nice, France, May, 1992; and U.S. Pat. No. 6,118,845, entitled "System And Methods For The Reduction And Elimination Of Image Artifacts In The Calibration Of X-Ray Imagers," issued Sep. 12, 2000, the contents of which are each hereby incorporated by reference.

While the fluoroscopic imaging device 12 is shown in FIG. 1, any other alternative 2D, 3D or 4D imaging modality may also be used. For example, any 2D, 3D or 4D imaging device, such as isocentric fluoroscopy, bi-plane fluoroscopy, ultrasound, computed tomography (CT), multi-slice computed tomography (MSCT), magnetic resonance imaging (MRI), high frequency ultrasound (HIFU), positron emission tomography (PET), positron emission tomography-computed tomography (PET/CT), high definition computed tomography (HDCT), dual source computed tomography, optical coherence tomography (OCT), intra-vascular ultrasound (IVUS), ultrasound, intra-operative CT or MRI, may also be used to acquire 2D, 3D or 4D pre-operative or real-time images or image data of the patient 14. The images may also be obtained and displayed in two, three or four dimensions. In more advanced forms, four-dimensional surface rendering of the heart or other regions of the body may also be achieved by incorporating heart data or other soft tissue data from an atlas map or from pre-operative image data captured by MRI, CT, or echocardiography modalities. A more detailed discussion on optical coherence tomography (OCT), is set forth in U.S. Pat. No. 5,740,808, issued Apr. 21, 1998, entitled "Systems And Methods For Guilding Diagnostic Or Therapeutic Devices In Interior Tissue Regions" which is hereby incorporated by reference.

Image datasets from hybrid modalities, such as positron emission tomography (PET) combined with CT, or single photon emission computer tomography (SPECT) combined with CT, could also provide functional image data superimposed onto anatomical data to be used to confidently reach target sights within the heart or other areas of interest. It should further be noted that the fluoroscopic imaging device 12, as shown in FIG. 1, provides a virtual bi-plane image using a single-head C-arm fluoroscope 12 by simply rotating the C-arm 16 about at least two planes, which could be orthogonal planes to generate two-dimensional images that can be converted to three-dimensional volumetric images. By acquiring images in more than one plane, an icon representing the location of a catheter or other instrument, introduced and advanced in the patient 14, may be superimposed in more than one view on display 36 allowing simulated bi-plane or even multi-plane views, including two and three-dimensional views.

These types of imaging modalities may provide certain distinct benefits and disadvantages for their use. For example, magnetic resonance imaging (MRI) is generally performed pre-operatively using a non-ionizing field. This type of imaging provides very good tissue visualization in three-dimensional form and also provides anatomical and functional information from the imaging. MRI imaging data is generally registers and compensates for motion correction using dynamic reference frames that are discussed herein.

Positron emission tomography (PET) imaging is generally a pre-operative imaging procedure that exposes the patient to some level of radiation to provide a 3D image. PET imaging provides functional information and also generally requires registration and motion correction using dynamic reference frames.

Computed tomography (CT) imaging is also generally a pre-operative technique that exposes the patient to a limited level of radiation. CT imaging, however, is a very rapid imaging procedure. A multi-slice CT system provides 3D images having good resolution and anatomical information. Again, CT imaging is generally registered and needs to account for motion correction via dynamic reference frames.

Fluoroscopy imaging is generally an intra-operative imaging procedure that exposes the patient to certain amounts of radiation to provide either two-dimensional or rotational three-dimensional images. Fluoroscopic images generally provide good resolution and anatomical information. Fluoroscopic images can be either manually or automatically registered and also need to account for motion correction using dynamic reference frames.

Ultrasound imaging is also generally an intra-operative procedure using a non-ionizing field to provide either 2D, 3D, or 4D imaging, including anatomical and blood flow information. Ultrasound imaging provides automatic registration and does not need to account for any motion correction.

The navigation system 10 further includes an electromagnetic navigation or tracking system 44 that includes a transmitter coil array 46, the coil array controller 48, a navigation probe interface 50, an electromagnetic catheter 52 or any other type of instrument and a dynamic reference frame 54. Further, it should further be noted that the entire tracking system 44 or parts of the tracking system 44 may be incorporated into the imaging device 12, including the work station 34 and radiation sensors 24. Incorporating the tracking system 44 will provide an integrated imaging and tracking system. Any combination of these components may also be incorporated into the imaging device 12, which again can include a fluoroscopic C-arm imaging device or any other appropriate imaging device.

The transmitter coil array 46 is shown attached to the receiving section 20 of the C-arm 16. However, it should be noted that the transmitter coil array 46 may also be positioned at any other location as well. For example, the transmitter coil array 46 may be positioned at the x-ray source 18, within or atop the OR table 56 positioned below the patient 14, on siderails associated with the table 56, or positioned on the patient 14 in proximity to the region being navigated, such as on the patient's chest. The transmitter coil array 46 includes a plurality of coils that are each operable to generate distinct electromagnetic fields into the navigation region of the patient 14, which is sometimes referred to as patient space. Representative electromagnetic systems are set forth in U.S. Pat. No. 5,913,820, entitled "Position Location System," issued Jun. 22, 1999, and U.S. Pat. No. 5,592,939, entitled "Method and System for Navigating a Catheter Probe," issued Jan. 14, 1997, each of which are hereby incorporated by reference.

The transmitter coil array 46 is controlled or driven by the coil array controller 48. The coil array controller 48 drives each coil in the transmitter coil array 46 in a time division multiplex or a frequency division multiplex manner. In this regard, each coil may be driven separately at a distinct time or all of the coils may be driven simultaneously with each being driven by a different frequency. Upon driving the coils in the transmitter coil array 46 with the coil array controller 48, electromagnetic fields are generated within the patient 14 in the area where the medical procedure is being performed, which is again sometimes referred to as patient space. The electromagnetic fields generated in the patient space induces currents in sensors 58 positioned in the catheter 52. These induced signals from the catheter 52 are delivered to the navigation probe interface 50 and subsequently forwarded to the coil array controller 48. The navigation probe interface 50 provides all the necessary electrical isolation for the navigation system 10. The navigation probe interface 50 also includes amplifiers, filters and buffers required to directly interface with the sensors 58 in catheter 52. Alternatively, the catheter 52 may employ a wireless communications channel as opposed to being coupled directly to the navigation probe interface 50.

The catheter 52 may be equipped with at least one, and generally multiple, localization sensors 58. The catheter 52 may also be a steerable catheter that includes a handle at a proximal end and the multiple location sensors 58 fixed to the catheter body and spaced axially from one another along the distal segment of the catheter 52. The catheter 52, as shown in FIG. 1, includes four localization sensors 58. The localization sensors 58 are generally formed as electromagnetic receiver coils, such that the electromagnetic field generated by the transmitter coil array 46 induces current in the electromagnetic receiver coils or sensors 58. The catheter 52 may also be equipped with one or more sensors, which are operable to sense various physiological signals. For example, the catheter 52 may be provided with electrodes for sensing myopotentials or action potentials. An absolute pressure sensor may also be included, as well as other electrode sensors. The catheter 52 may also be provided with an open lumen to allow the delivery of a medical device or pharmaceutical/cell/gene agents. For example, the catheter 52 may be used as a guide catheter for deploying a medical lead, such as a cardiac lead for use in cardiac pacing and/or defibrillation or tissue ablation. The open lumen may alternatively be used to locally deliver pharmaceutical agents, cell, or genetic therapies. A representative catheter which may be used is that which is disclosed in U.S. Patent Publication No. 2004/0097805 entitled "Navigation System for Cardiac Therapies", filed Jul. 14, 2003, which is hereby incorporated by reference.

In an alternate embodiment, the electromagnetic sources or generators may be located within the catheter 52 and one or more receiver coils may be provided externally to the patient 14, forming a receiver coil array similar to the transmitter coil array 46. In this regard, the sensor coils 58 would generate electromagnetic fields, which would be received by the receiving coils in the receiving coil array similar to the transmitter coil array 46. Other types of localization sensors or systems may also be used, which may include an emitter, which emits energy, such as light, sound, or electromagnetic radiation, and a receiver that detects the energy at a position away from the emitter. This change in energy, from the emitter to the receiver, is used to determine the location of the receiver relative to the emitter. Other types of tracking systems include optical, acoustic, electrical field, RF and accelerometers. Accelerometers enable both dynamic sensing due to motion and static sensing due to gravity. An additional representative alternative localization and tracking system is set forth in U.S. Pat. No. 5,983,126, entitled "Catheter Location System and Method," issued Nov. 9, 1999, which is hereby incorporated by reference. Alternatively, the localization system may be a hybrid system that includes components from various systems.

The dynamic reference frame 54 of the electromagnetic tracking system 44 is also coupled to the navigation probe interface 50 to forward the information to the coil array controller 48. The dynamic reference frame 54 is a small magnetic field detector that is designed to be fixed to the patient 14 adjacent to the region being navigated so that any movement of the patient 14 is detected as relative motion between the transmitter coil array 46 and the dynamic reference frame 54. This relative motion is forwarded to the coil array controller 48, which updates registration correlation and maintains accurate navigation, further discussed herein. The dynamic reference frame 54 can be configured as a pair of orthogonally oriented coils, each having the same center or may be configured in any other non-coaxial coil configuration. The dynamic reference frame 54 may be affixed externally to the patient 14, adjacent to the region of navigation, such as on the patient's chest, as shown in FIG. 1 or on the patient's back. The dynamic reference frame 54 can be affixed to the patient's skin, by way of a stick-on adhesive patch. The dynamic reference frame 54 may also be removably attachable to fiducial markers 60 also positioned on the patient's body as further discussed herein.

Alternatively, the dynamic reference frame 54 may be internally attached, for example, to the wall of the patient's heart or other soft tissue using a temporary lead that is attached directly to the heart. This provides increased accuracy since this lead will track the regional motion of the heart. Gating, as further discussed herein, will also increase the navigational accuracy of the system 10. An exemplary dynamic reference frame 54 and fiducial marker 60, is set forth in U.S. Pat. No. 6,381,485, entitled "Registration of Human Anatomy Integrated for Electromagnetic Localization," issued Apr. 30, 2002, which is hereby incorporated by reference. It should further be noted that multiple dynamic reference frames 54 may also be employed. For example, an external dynamic reference frame 54 may be attached to the chest of the patient 14, as well as to the back of the patient 14. Since certain regions of the body may move more than others due to motions of the heart or the respiratory system, each dynamic reference frame 54 may be appropriately weighted to increase accuracy even further. In this regard, the dynamic reference frame 54 attached to the back may be weighted higher than the dynamic reference frame 54 attached to the chest, since the dynamic reference frame 54 attached to the back is relatively static in motion.

The catheter and navigation system 10 further includes a gating device or an ECG or electrocardiogram 62, which is attached to the patient 14, via skin electrodes 64, and in communication with the coil array controller 48. Respiration and cardiac motion can cause movement of cardiac structures relative to the catheter 52, even when the catheter 52 has not been moved. Therefore, localization data may be acquired on a time-gated basis triggered by a physiological signal. For example, the ECG or EGM signal may be acquired from the skin electrodes 64 or from a sensing electrode included on the catheter 52 or from a separate reference probe. As will be discussed more fully below, a characteristic of this signal may be used as to gate or trigger image acquisition during the imaging phase with the imaging device 12. By event gating at a point in a cycle the image data and/or the navigation data, the icon of the location of the catheter 52 relative to the heart at the same point in the cardiac cycle may be displayed on the display 36, further discussed herein.

Additionally or alternatively, a sensor regarding respiration may be used to trigger data collection at the same point in the respiration cycle. Additional external sensors can also be coupled to the navigation system 10. These could include a capnographic sensor that monitors exhaled $CO_2$ concentration. From this, the end expiration point can be easily determined. The respiration, both ventriculated and spontaneous causes an undesirable elevation or reduction, respectively, in the baseline pressure signal. By measuring systolic and diastolic pressures at the end expiration point, the coupling of respiration noise is minimized. As an alternative to the $CO_2$ sensor, an airway pressure sensor can be used to determine end expiration.

Briefly, the navigation system 10 operates as follows. The navigation system 10 creates a translation map between all points in the radiological image generated from the imaging device 12 and the corresponding points in the patient's anatomy in patient space. After this map is established, whenever a tracked instrument, such as the catheter 52 or pointing device is used, the work station 34, in combination with the coil array controller 48 and the C-arm controller 28, uses the translation map to identify the corresponding point on the pre-acquired image, which is exhibited on display 36. This identification is known as navigation or localization. An icon representing the localized point or instruments are shown on the display 36 within several two-dimensional image planes, as well as on three and four dimensional images and models.

To enable navigation, the navigation system 10 must be able to detect both the position of the patient's anatomy and the position of the catheter 52 or other surgical instrument. Knowing the location of these two items allows the navigation system 10 to compute and display the position of the catheter 52 in relation to the patient 14 on the radiological images. The tracking system 44 is employed to track the catheter 52 and the anatomy simultaneously.

The tracking system 44 essentially works by positioning the transmitter coil array 46 adjacent to the patient space to generate a low-energy magnetic field generally referred to as a navigation field. Because every point in the navigation field or patient space is associated with a unique field strength, the electromagnetic tracking system 44 can determine the position of the catheter 52 by measuring the field strength at the sensor 58 location. The dynamic reference frame 54 is fixed to the patient 14 to identify the location of the patient in the navigation field. The electromagnetic tracking system 44 continuously recomputes the relative position of the dynamic reference frame 54 and the catheter 52 during localization and relates this spatial information to patient registration data to enable image guidance of the catheter 52 within the patient 14.

Patient registration is the process of determining how to correlate the position of the instrument or catheter 52 on the patient 14 to the position on the diagnostic or pre-acquired images. To register the patient 14, the physician or user may use point registration by selecting and storing particular points from the pre-acquired images and then touching the corresponding points on the patient's anatomy with a pointer probe 66. The navigation system 10 analyzes the relationship between the two sets of points that are selected and computes a match, which correlates every point in the image data with its corresponding point on the patient's anatomy or the patient space. The points that are selected to perform registration are the fiducial arrays or landmarks 60. Again, the landmarks or fiducial points 60 are identifiable on the images and identifiable and accessible on the patient 14. The landmarks 60 can be artificial landmarks 60 that are positioned on the patient 14 or anatomical landmarks that can be easily identified in the image data. The system 10 may also perform registration using anatomic surface information or path information, further discussed herein. The system 10 may also perform 2D to 3D registration by utilizing the acquired 2D images to register 3D volume images by use of contour algorithms, point algorithms or density comparison algorithms, as is known in the art. An exemplary 2D to 3D registration procedure, as set forth in U.S. Patent Publication No. 2004/0215071, entitled "Method and Apparatus for Performing 2D to 3D Registration," which is hereby incorporated by reference. The registration process may also be synched to an anatomical function, for example, by the use of the ECG device 62, further discussed herein.

In order to maintain registration accuracy, the navigation system 10 continuously tracks the position of the patient 14 during registration and navigation. This is because the patient 14, dynamic reference frame 54, and transmitter coil array 46 may all move during the procedure, even when this movement is not desired. Therefore, if the navigation system 10 did not track the position of the patient 14 or area of the anatomy, any patient movement after image acquisition would result in inaccurate navigation within that image. The dynamic reference frame 54 allows the electromagnetic tracking system 44 to register and track the anatomy. Because the dynamic reference frame 54 is attached to the patient 14, any movement of the anatomy or the transmitter coil array 46 is detected as the relative motion between the transmitter coil array 46 and the dynamic reference frame 54. This relative motion is communicated to the coil array controller 48, via the navigation probe interface 50, which updates the registration correlation to thereby maintain accurate navigation.

Figure 3:
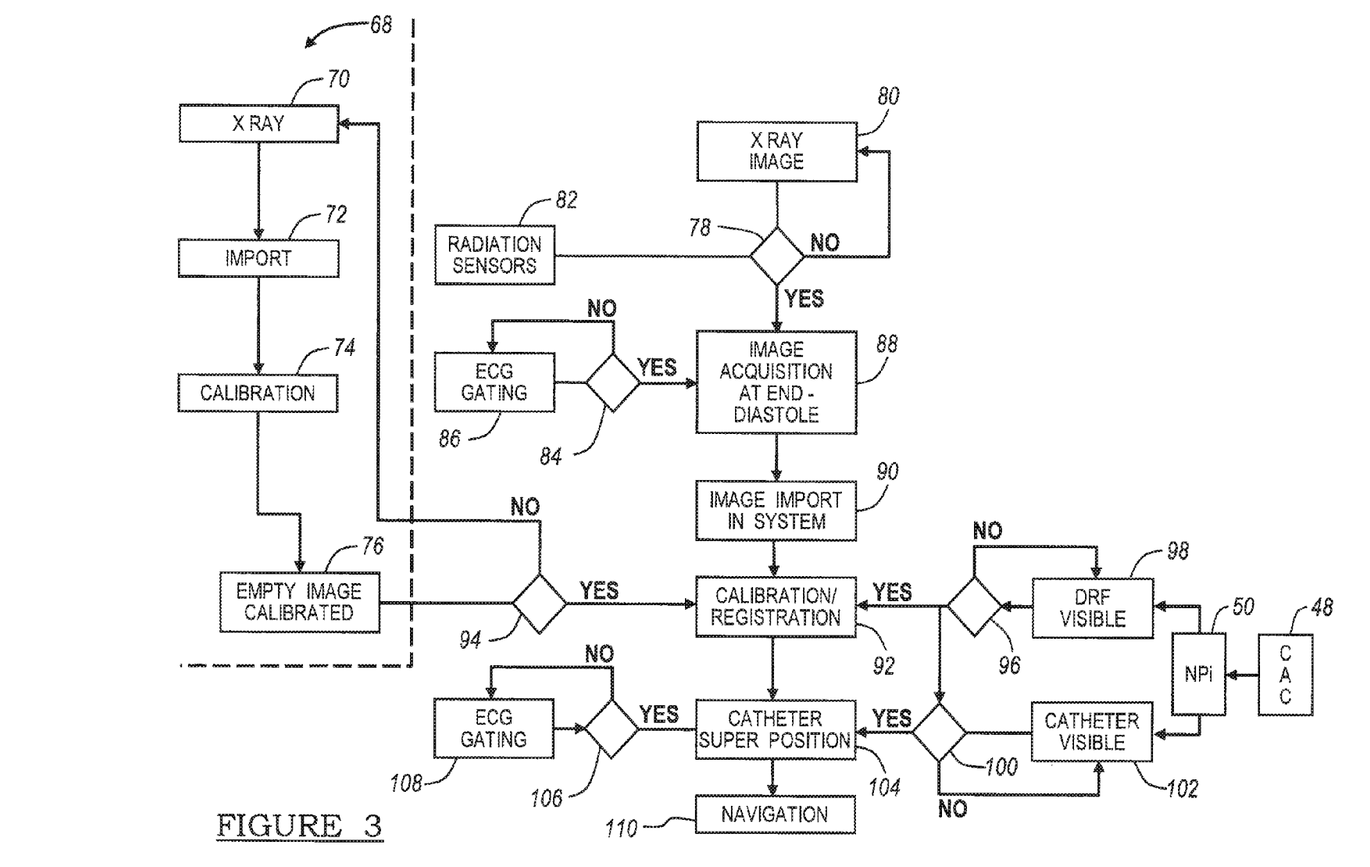
FIG. 3 is a logic block diagram illustrating a method for navigating a catheter during cardiac therapy.

Turning now to FIG. 3, a logic flow diagram illustrating an exemplary operation of the navigation system 10 is set forth in further detail. First, should the imaging device 12 or the fluoroscopic C-arm imager 12 not include a digital receiving section 20, the imaging device 12 is first calibrated using the calibration process 68. The calibration process 68 begins at block 70 by generating an x-ray by the x-ray source 18, which is received by the x-ray receiving section 20. The x-ray image 70 is then captured or imported at import block 72 from the C-arm controller 28 to the work station 34. The work station 34 performs intrinsic calibration at calibration block 74, as discussed above, utilizing the calibration markers 26, shown in FIGS. 2a and 2b. This results in an empty image being calibrated at block 76. This calibrated empty image is utilized for subsequent calibration and registration, further discussed herein.

Once the imaging device 12 has been calibrated, the patient 14 is positioned within the C-arm 16 between the x-ray source 18 and the x-ray receiving section 20. The navigation process begins at decision block 78 where it is determined whether or not an x-ray image of the patient 14 has been taken. If the x-ray image has not been taken, the process proceeds to block 80 where the x-ray image is generated at the x-ray source 18 and received at the x-ray receiving section 20. In some embodiments, when the x-ray source 18 is generating x-rays, the radiation sensors 24 identified in block 82 may activate to identify that the x-ray image 80 is being taken. This enables the tracking system 44 to identify where the C-arm 16 is located relative to the patient 14 when the image data is being captured. In some embodiments, however, the tracking system 44 may not need to be triggered by the radiation sensors 24.

The process then proceeds to decision block 84 where it is determined if the x-ray image acquisition will be gated to physiological activity of the patient 14. If so, the image device 12 will capture the x-ray image at this desired gating time. For example, the physiological change may be the beating heart, which is identified by ECG gating at block 86. The ECG gating enables the x-ray image acquisition to take place at the end of diastole at block 88, as will be more fully discussed below. Diastole is the period of time between contractions of the atria or the ventricles during which blood enters the relaxed chambers from systemic circulation and the lungs. Diastole is often measured as the blood pressure at the instant of maximum cardiac relaxation. ECG gating of myocardial injections also enables optimal injection volumes and injection rates to achieve maximum cell retention. The optimal injection time period may go over one heart cycle. During the injection, relative motion of the catheter tip to the endocardial surface needs to be minimized. Conductivity electrodes at the catheter tip may be used to maintain this minimized motion. Also, gating the delivery of volumes can be used to increase or decrease the volume delivered over time (i.e., ramp-up or ramp-down during cycle). Again, the image may be gated to any physiological change like the heartbeat, respiratory functions, etc. The image acquired at block 88 is then imported to the work station 34 at block 90. If it is not desired to physiologically gate the image acquisition cycle, the process will proceed from the x-ray image block 80 directly to the image import block 90.

Once the image is received and stored in the work station 34, the process proceeds to calibration and registration at block 92. First, at decision block 94, it is determined whether the imaging device 12 has been calibrated, if so, the empty image calibration information from block 76 is provided for calibration registration at block 92. The empty image calibration information from block 76 is used to correct image distortion by establishing projective transformations using known calibration marker locations (see FIGS. 2a and 2b). Calibration registration 92 also requires tracking of the dynamic reference frame 54. In this regard, it is first determined at decision block 96 whether or not the dynamic reference frame is visible, via block 98. With the dynamic reference frame 54 visible or in the navigation field and the calibration information provided, the work station 34 and the coil array controller 48, via the navigation probe interface 50 performs the calibration registration 92 functions. In addition to monitoring the dynamic reference frame 54, the fiducial array or landmarks 60 may also be used for image registration.

Once the navigation system 10 has been calibrated and registered, navigation of an instrument, such as the catheter 52 is performed. In this regard, once it is determined at decision block 100 that the catheter 54 is visible or in the navigation field at block 102, an icon representing the catheter 52 is superimposed over the pre-acquired images at block 104. Should it be determined to match the superimposed image of the catheter 52 with the motion of the heart at decision block 106, ECG gating at block 108 is performed. The catheter 52 may then be navigated, via navigation block 110 throughout the anatomical area of interest in the patient 14.

Figure 4:
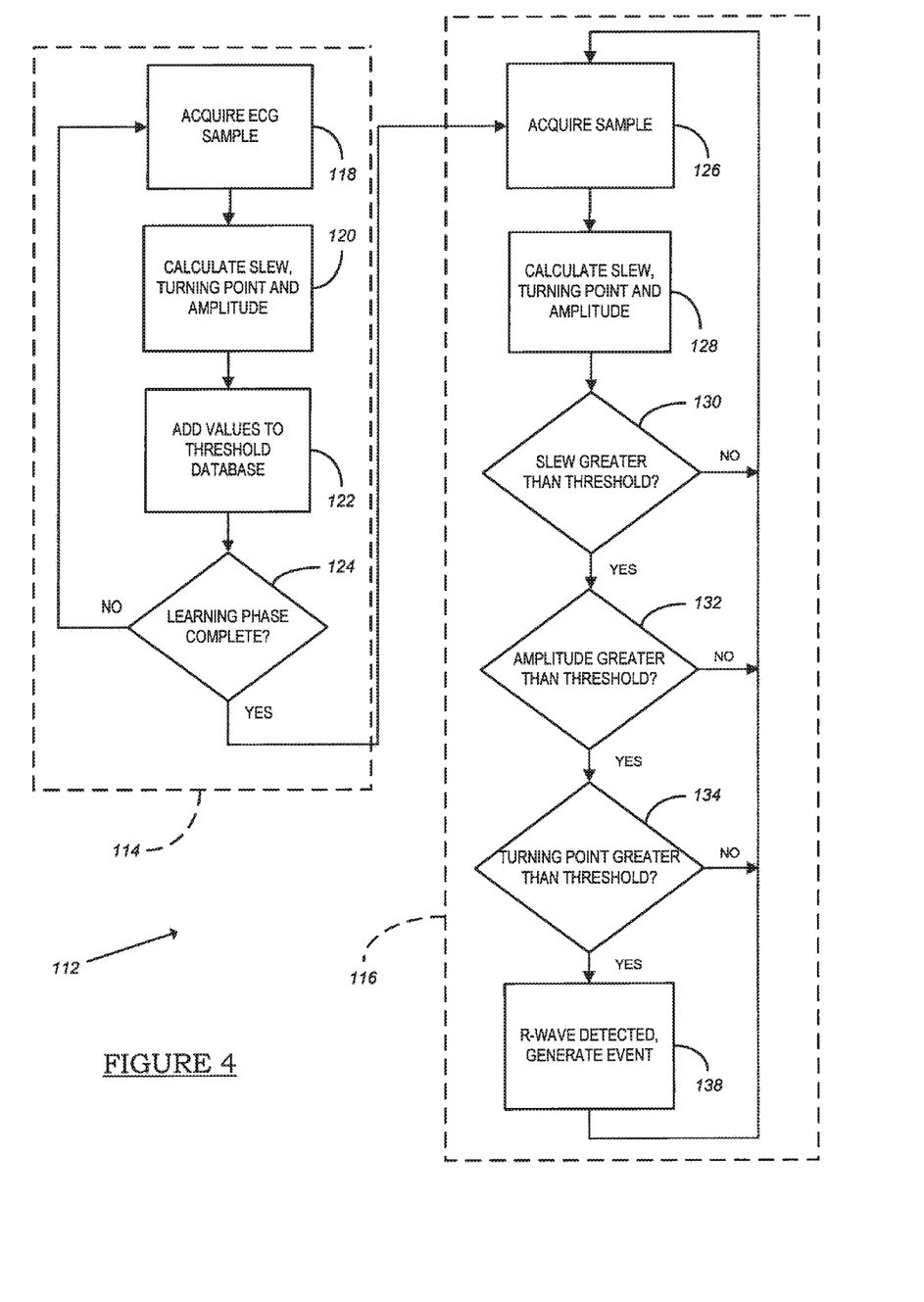
FIG. 4 is a logic block diagram illustrating the R-wave detector associated with the method for navigating a catheter during cardiac therapy as shown in FIG. 3.
Figure 5:
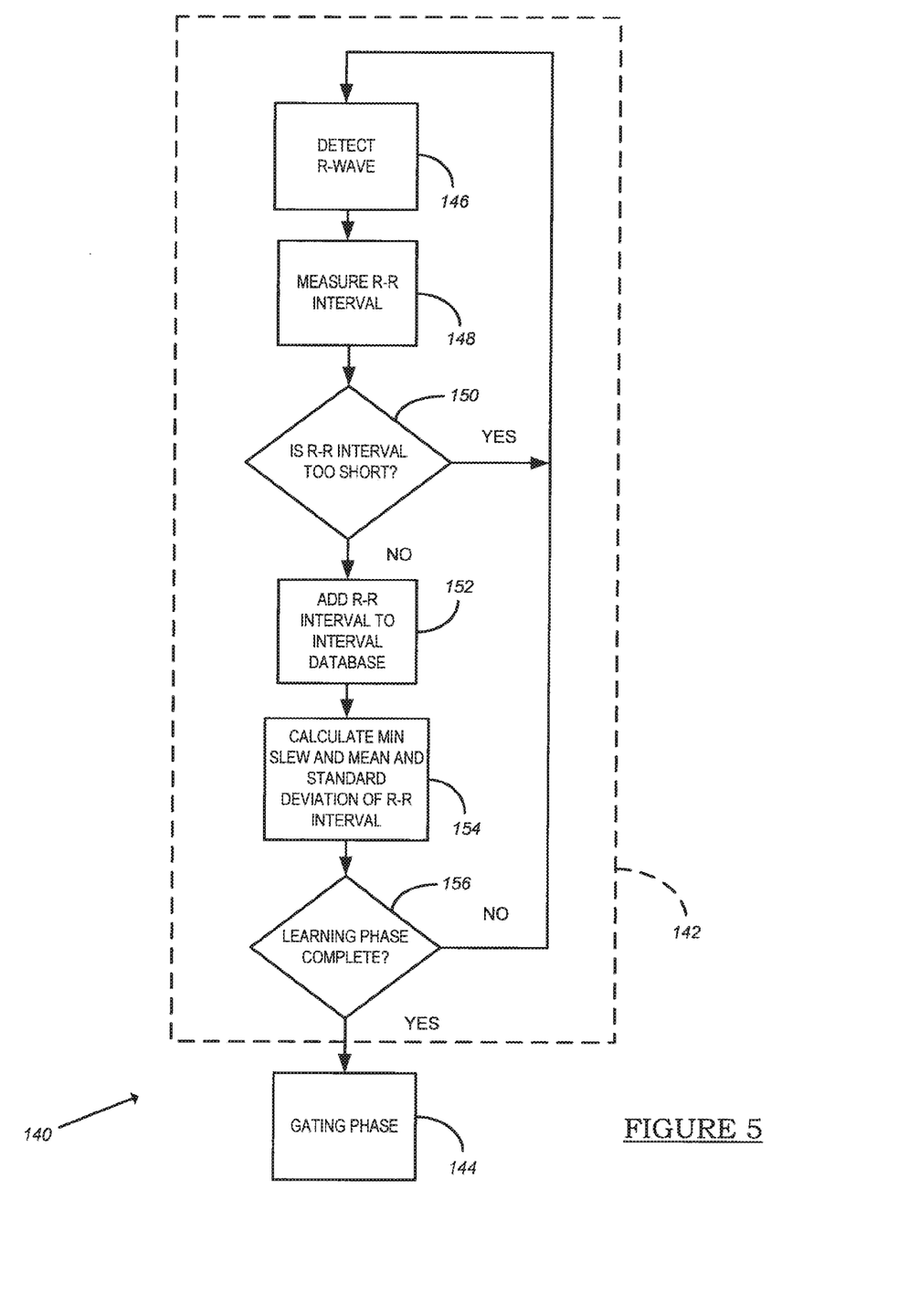
FIG. 5 is a logic block diagram illustrating the diastole detector associated with the method for navigating a catheter during cardiac therapy as shown in FIG. 3.
Figure 6:
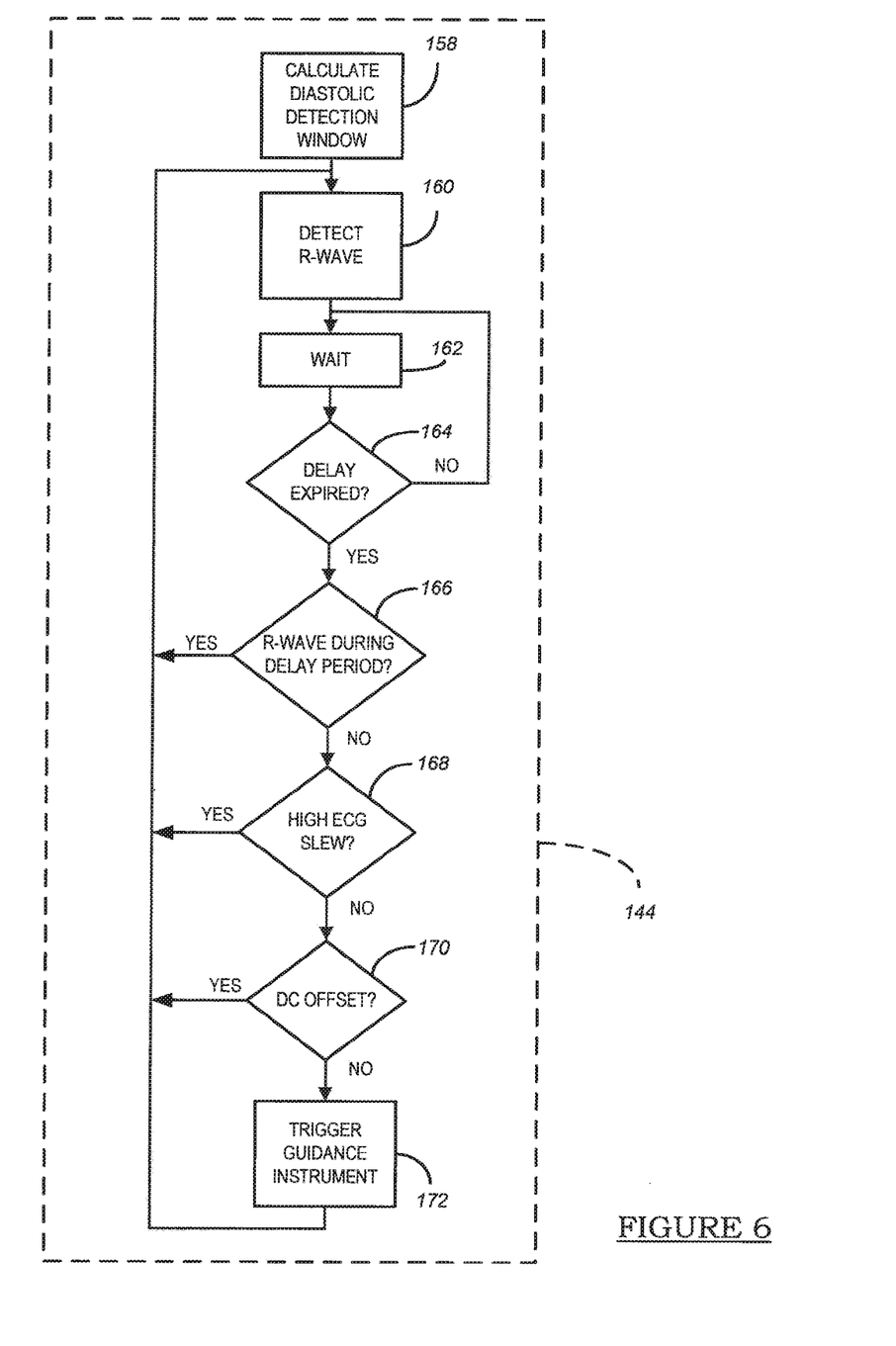
FIG. 6 is a logic block diagram illustrating the gating phase of the diastole detector illustrated in FIG. 5.
Figure 7:
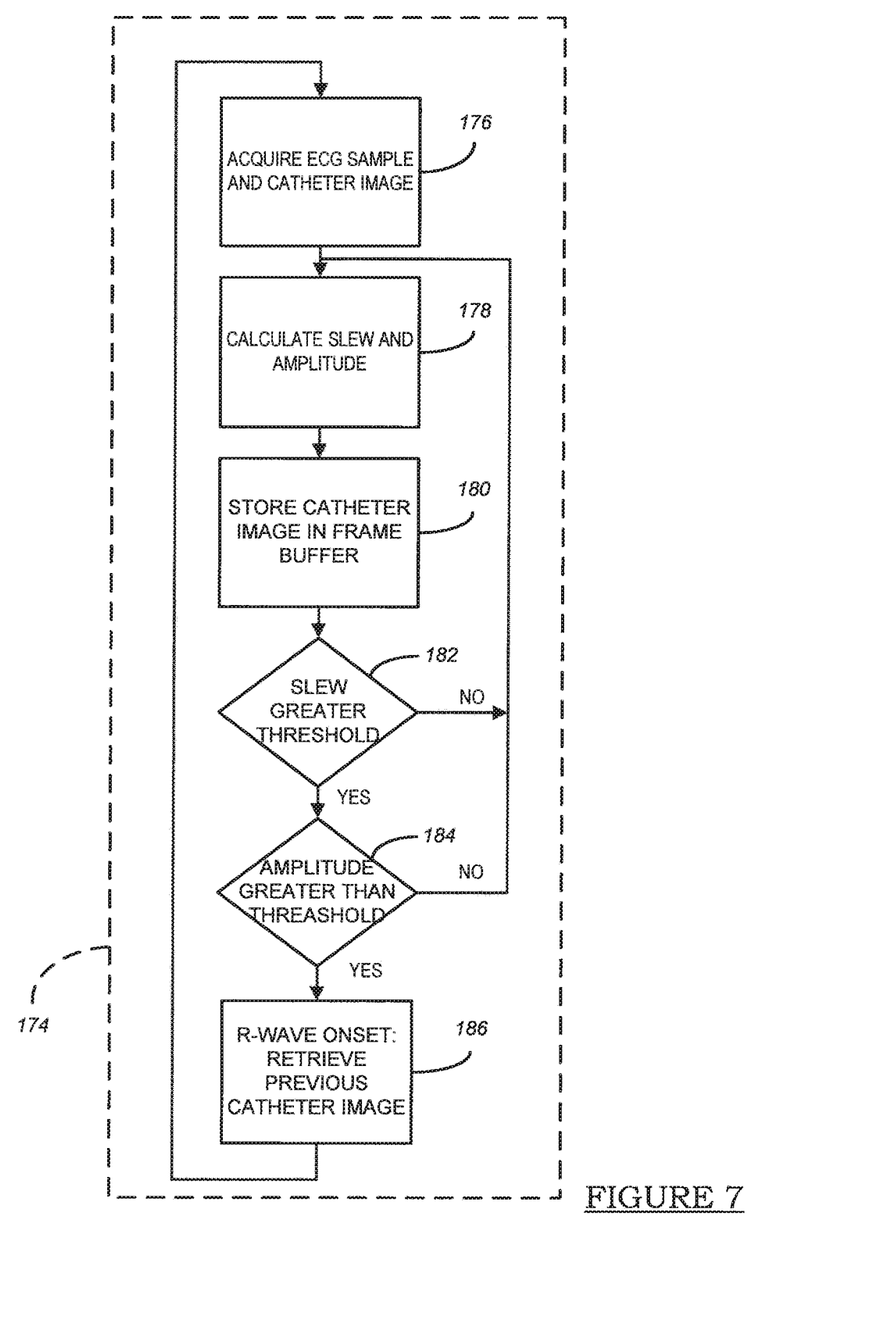
FIG. 7 is a logic block diagram illustrating an onset R-wave detector associated with a method for image guiding an instrument according to the present teachings.

The ECG gating at blocks 86 and 108 will now be fully described with respect to FIGS. 4-7. The ECG gating signals generated by blocks 86 and 108 may use different characteristics of the ECG signal to generate gating signal, and may include the use of an R-wave detector 112 as shown in FIG. 4, or a diastole detector 140 as shown in FIGS. 5 and 6. In addition, the ECG gating signals generate at blocks 86 and 108 may include the use of an onset R-wave detector as shown in FIG. 7. Each of these detectors for ECG gating at blocks 86 and 108 will now be described in greater detail.

As discussed above, the ECG gating performed at blocks 86 and 108 may include an R-wave detector 112 as illustrated in FIG. 4. The R-wave detector 112 has two phases: a learning phase 114 and a detection phase 116. In this regard, the threshold characteristics associated with the ECG signals from the patient are initially acquired during the learning phase 114. Once the learning phase 114 has been completed, the detection phase 116 associated with the R-wave detector 112 is performed which generates a gating signal by comparing the characteristics of the current ECG signal to the thresholds calculated during the learning phase 114.

As shown in FIG. 4, the learning phase 114 of the R-wave detector 112 includes block 118 in which the ECG signal is initially acquired. Once the ECG signal is acquired at block 118, the learning phase 114 calculates certain characteristics of the ECG signal at block 120 including slew, turning point and amplitude. The slew of the ECG signal is the slope of the ECG signal taken by selecting 10 samples within a 25 millisecond window. The turning point represents the running sum of 20 samples taken at a rate of 400 samples per second and represents a near term extrema of the ECG signal. The amplitude determined at block 120 is simply the amplitude of a ECG signal.

Once the slew, turning point and amplitude of the ECG signal are calculated at the block 120, the learning phase 114 of the R-wave detector 112 adds these values to a threshold database at block 122. The threshold database contains a 10 period moving average of the slew, turning point and amplitude of the ECG signals. Once the values for slew, turning point and amplitude have been added to the threshold database at block 122, the learning phase 114 determines whether the learning phase is completed at block 124 by calculating whether 10 cardiac cycles have occurred since the learning phase 114 began. If 10 cardiac cycles have occurred, then the R-wave detector 112 initiates the detection phase 116. However, if fewer then 10 cardiac cycles have occurred, the learning phase 114 acquires another ECG signal at block 118.

As discussed above, if the learning phase 114 has obtained information from 10 cardiac cycles, the R-wave detector 112 then initiates the detection phase 116. As shown in FIG. 4, the detection phase 116 initially acquires the current ECG signal at block 126. After the current ECG signal is acquired at block 126, the detection phase 116 then calculates the slew, turning point and amplitude of the current ECG signal at block 128. The slew, turning point and amplitude are calculated in the same manner as discussed above with respect to block 120.

After the slew, turning point and amplitude have been calculated at block 128, the detection phase 116 then determines whether the slew of the current ECG signal is greater than a threshold at block 130. In this regard, the slew threshold may be about 0.9 times the average slew that is stored in the threshold database at block 122 during the learning phase 114. It will be understood, however, that other values for the slew threshold may be used. If the slew of the current ECG signal is greater than the threshold as determined at block 130, then the detection phase 116 determines whether the amplitude of the current ECG signal is greater than an amplitude threshold. In this regard, the detection phase 116 determines whether the amplitude of the current ECG signal is greater than about 0.9 times the average amplitude of the ECG signal stored in the threshold database at block 122 during the learning phase 114. If the amplitude of the current ECG signal is less than the amplitude threshold as compared at block 132, a new sample is acquired at block 126. However, if the amplitude of the current ECG signal is greater than the amplitude threshold as determined by block 132, then the detection phase 116 compares at block 134 the turning point of the current ECG signal to the turning point threshold. In this regard, the detection phase 116 determines whether the turning point of the current ECG signal is greater or lesser than the turning point threshold stored in the threshold database at block 122. If the turning point of the current ECG signal is less than the turning point threshold determined at block 134, then the detection phase 116 assumes that the current ECG signal does not contain an R-wave and therefore a new sample is acquired at block 126.

However, if the turning point of the current ECG sample is greater than the turning point threshold as determined at block 134, then the detection phase 116 assumes that the ECG signal contains an R-wave. When this occurs, a gating signal is generated by block 138 following a delay period from onset of the R-wave that was detected. For example, the detection phase 116 may generate a gating signal after a delay of 70% of the interval between adjacent R-waves (hereinafter the "R-R interval"). In this case, if the temporal spacing between two adjacent R-waves is 670 milliseconds, a gating signal may be generated after a delay of approximately 469 milliseconds after the R-wave that was detected. However, other delay periods may be suitable.

As discussed above, the ECG gating at blocks 86 and 108 may also include the use of a diastole detector 140 as illustrated in FIGS. 5 and 6. The diastole detector 140 has a learning phase 142 and a gating phase 144. The learning phase 142 of the diastole detector 140 calculates the mean and standard deviation of the R-R interval as will be fully discussed below. The gating phase 144 of the diastole detector 140 is used for confirming that a diastolic region of the ECG signal is present before causing a gating signal to be generated at blocks 86 and 108. The learning phase 142 and the gating phase 144 of the diastole detector 140 will now be described in greater detail.

In the learning phase 142 of the diastole detector 140, the presence of an R-wave is first detected at block 146. In this regard, the R-wave detector 112, as shown in FIG. 4, may be used for detecting the presence of an R-wave. However, other suitable R-wave detectors may be used. After the R-wave is detected at block 146, the time interval between the current R-wave and immediately proceeding R-wave is calculated at block 148. After the R-R interval has been calculated at block 148, the learning phase 142 determines whether the R-R interval is too short at block 150 (e.g., when arrhythmias may have occurred). In one embodiment, the R-R interval may be too short if the R-R interval is less than about 300-350 milliseconds. If the R-R interval is too short as determined by block 150, the learning phase 142 then waits until the next R-wave occurs as indicated by block 146. If the R-R interval is sufficiently long as determined by block 150, the learning phase 142 then adds the R-R interval as well as the slew to the interval database at block 152. Once the R-R interval is added to the interval database, the learning phase 142 then calculates the mean and standard deviation of the R-R intervals stored in the database, as well as determines the minimum slew of the slew data of the ECG signals that have been evaluated during the learning phase 142. After the mean and standard deviation of the R-R interval are calculated, the diastole detector 140 determines whether the learning phase is complete at block 156. The learning phase may be determined to be complete after it has processed 10 cardiac cycles of sufficient length, as described above.

Once the learning phase 156 is complete, the gating phase of the diastole detector 140 is initiated. In this regard, the gating phase 144 initially determines the location of a diastolic detection window. The diastolic detection window is the region of the ECG signal in which the heart is believed to be in diastole, and in which ECG signals are evaluated to confirm the heart is in diastole. The width of the diastolic detection window may be about 75 milliseconds, though other suitable widths may be used. The location of the diastolic detection window with respect to the current ECG signal may be determined by the variation of the R-R interval calculated during the learning phase 142. In this regard, if there is a relatively high standard deviation in the R-R interval as calculated at block 154, there is a relatively high likelihood of that the ECG signal may contain arrhythmias or ectopic beats. Under these circumstances, it may be desirable to center the diastolic detection window at approximately 45% of the R-R interval following the onset of an R-wave. In contrast, if the standard deviation of the R-R interval calculated at block 154 is relatively small, then it is likely that the ECG signal corresponds to normal sinus rhythms. In this case, the diastolic detection window may be centered later in the cardiac cycle, such as at 70% (or about 62% to about 80%) of the duration R-R interval following the detection of an R-wave. It is to be understood, however, that the diastolic detection window may be centered at other suitable locations.

After the location of the diastolic detection window is determined at 158, the gating phase 144 detects the presence of an R-wave block 160 (such as by using the R-wave detector 112). Once an R-wave is detected at block 160, the current ECG signals located in the diastolic detection window are recorded during the diastolic detection window by waiting until the diastolic detection window opens by means of blocks 162 and 164. Once the diastolic detection window has opened, the gating phase 144 determines whether an R-wave has occurred within the diastolic detection window at block 166. This may be performed using the R-wave detector 112 shown in FIG. 4, though other suitable R-wave detectors may be used. If an R-wave has occurred during the diastolic detection window, the gating phase 144 may prevent the generation of a gating signal at blocks 86 and 108 by waiting until the occurrence of the next R-wave as indicated by block 160. If no R-wave has been detected during the diastolic detection window as determined by block 166, then the gating phase 144 may determine whether the slew associated with the current ECG signal is relatively high. In this regard, the gating phase 144 may select 30 samples (at a rate of 400 samples per second) and determine whether the slew is greater than 5 times the minimum slew as calculated at block 154. If the slew of the ECG signal is sufficiently high, the gating phase 144 may not cause the generation of a gating signal from blocks 86 and 108 but waits until the next R-wave is detected at block 160.

If the slew of the current ECG signal is not high as determined at block 168, the gating phase 144 may determine whether there is a DC offset associated with the current ECG signal. If there is a DC offset to the current ECG signal, then the gating phase 144 may also not cause the generation of a gating signal at blocks 86 and 108 but waits until another R-wave is detected at block 160. If there is no DC offset, then the gating phase 144 may trigger the generation of a gating signal at blocks 86 and 108 as indicated by block 172.

It will be appreciated that the check for DC offset at block 170 may occur during normal sinus rhythms and may not generally be necessary when arrhythmias may be present. In addition, also during normal sinus rhythms, once a gating signal is generated by blocks 86 and 108, the gating phase 144 may prevent the generation of another gating signal from blocks 86 and 108 for a period of time (such as, for example, 70% of the R-R interval following the next R-wave).

As discussed above, the ECG gating at blocks 86 and 108 can also include an onset R-wave detector 174 as illustrated in FIG. 7. The onset R-wave detector 174 is used for sensing the onset of an R-wave during a cardiac cycle, and causing the navigation system to display the previously acquired image of the catheter when the heart was in diastole. As indicated by block 176, the onset R-wave detector 174 initially acquires the ECG signal as well as the catheter image. Once the ECG signal and catheter image has been acquired at block 176, the onset R-wave detector 174 may calculate the slew and amplitude characteristics of the ECG signal at block 178. In addition, the onset R-wave detector 174 may store the catheter image in a frame buffer at block 180. If the slew or the amplitude of the ECG signal exceed respectively thresholds (as determined by blocks 182 and 184), the onset R-wave detector 174 determines that R-wave onset has occurred and, therefore, retrieves the previous catheter image from the frame buffer for use to register the image of the catheter as illustrated by block 186. If either of the slew or the amplitude are not greater than their respective thresholds as determined by block 182 and 184, then the current image is used for purposes of registration and a new ECG signal and catheter image are then obtained at block 176.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. An image guided navigation system for guiding an instrument through a patient, said image guided navigation system comprising:
an anatomical gating device operable to sense diastole in a cardiac cycle, to define a diastolic detection window and to generate a gating signal indicative thereof, the diastolic detection window comprising a delay period following an R-wave;
an imaging device operable to capture image data of a region of the patient in which the instrument is located, responsive to the gating signal;
a display operable to display the captured image data of the region of the patient,
the anatomical gating device further:
configured to detect whether an R-wave has occurred within the diastolic detection window;
determine whether high slew is associated with an ECG signal,
determine whether a DC offset is associated with the ECG signal within the diastolic detection window if no R-wave has been detected during the diastolic detection window; and
generate the gating signal in response to lack of a DC offset in conjunction with lack of high slew associated with the ECG signal within the diastolic detection window.

2. The image guided navigation system as set forth in claim 1, the anatomical gating device operable to detect the presence of an R-wave by comparing at least one characteristic of the ECG signal to at least one corresponding threshold, the at least one characteristic selected from the group comprising of slew, turning point and amplitude.

3. The image guided navigation system as set forth in claim 1, wherein the anatomical gating device is operable to detect the onset of systole by calculating slew, amplitude and turning point of an ECG signal to determine the presence of an R-wave in the ECG signal, and generate a diastolic detection window in response to the variability of the interval between adjacent R-waves in the ECG signal.

4. The image guided navigation system as set forth in claim 1 wherein said imaging device is selected from a group of 2D, 3D or 4D imaging devices comprising a C-arm fluoroscopic imager, a magnetic resonance imager (MRI), a computed tomography (CT) imager, a positron emission tomography (PET) imager, an isocentric fluoroscopy imager, a bi-plane fluoroscopy imager, an ultrasound imager, a multi-slice computed tomography (MSCT) imager, positron emission tomography-computed tomography (PET/CT), high definition computed tomography (HDCT), dual source computed tomography, a high-frequency ultrasound (HIFU) imager, an optical coherence tomography (OCT) imager, an intra-vascular ultrasound imager (IVUS), an intra-operative CT imager, an intra-operative MRI imager, a single photon emission computer tomography (SPECT) imager, and a combination thereof.

5. The image guided navigation system as set forth in claim 1, wherein said instrument is operable to deliver a therapy to the patient, the therapy is selected from a group comprising lead placement, drug delivery, gene delivery, cell delivery, ablation, mitral valve repair, aortic valve repair, leadless pacemaker placement, leadless pressure sensor placement, and a combination thereof.

6. The image guided navigation system as set forth in claim 1, wherein said instrument is selected from a group comprising a catheter, a guide wire, a stylet, an insert, a needle and a combination thereof.

7. An image guided navigation system for guiding an instrument through a patient, said image guided navigation system comprising:
an anatomical gating device operable to sense diastole in a cardiac cycle, to define a diastolic detection window and to generate a gating signal indicative thereof, the diastolic detection window comprising a delay period following an R-wave;
an imaging device operable to capture image data of a region of the patient in which the instrument is located;
a tracking device operable to track the position of the instrument in the region of the patient, responsive to the gating signal;
a controller in communication with said anatomical gating device, said imaging device and said tracking device and operable to display the position of the instrument within the region of the patient;
the anatomical gating device further configured to:
detect whether an R-wave has occurred within the diastolic detection window;
determine whether high slew is associated with an ECG signal, determine whether a DC offset is associated with an ECG signal within the diastolic detection window if no R-wave has been detected during the diastolic detection window; and generate the gating signal in response to lack of a DC offset in conjunction with lack of high slew associated with the ECG signal within the diastolic detection window.

8. The image guided navigation system as set forth in claim 7, the anatomical gating device operable to detect the presence of an R-wave by comparing at least one characteristic of the ECG signal to at least one corresponding threshold, the at least one characteristic selected from the group comprising of slew, turning point and amplitude.

9. The image guided navigation as set forth in claim 7, wherein the anatomical gating device is operable to detect the onset of systole by calculating slew, amplitude and turning point of an ECG signal to determine the presence of an R-wave in the ECG signal, and generate a diastolic detection window in response to the variability of the interval between adjacent R-waves in the ECG signal.

10. The image guided navigation system as set forth in claim 7 wherein said imaging device is selected from a group of 2D, 3D or 4D imaging devices comprising a C-arm fluoroscopic imager, a magnetic resonance imager (MRI), a computed tomography (CT) imager, a positron emission tomography (PET) imager, an isocentric fluoroscopy imager, a bi-plane fluoroscopy imager, an ultrasound imager, a multi-slice computed tomography (MSCT) imager, positron emission tomography-computed tomography (PET/CT), high definition computed tomography (HDCT), dual source computed tomography, a high-frequency ultrasound (HIFU) imager, an optical coherence tomography (OCT) imager, an intra-vascular ultrasound imager (IVUS), an intra-operative CT imager, an intra-operative MRI imager, a single photon emission computer tomography (SPECT) imager, and a combination thereof.

11. The image guided navigation system as set forth in claim 7, wherein said instrument is operable to deliver a therapy to the patient, the therapy is selected from a group comprising lead placement, drug delivery, gene delivery, cell delivery, ablation, mitral valve repair, aortic valve repair, leadless pacemaker placement, leadless pressure sensor placement, and a combination thereof.

12. The image guided navigation system as set forth in claim 7, wherein said instrument is selected from a group comprising a catheter, a guide wire, a stylet, an insert, a needle and a combination thereof.

\* \* \* \* \*